United States Patent
Smith et al.

(10) Patent No.: US 7,719,414 B1
(45) Date of Patent: May 18, 2010

(54) ELECTRONIC MEDIC ALERT

(75) Inventors: Keith Shane Smith, Rome, GA (US); Jeffrey Clinton Mikan, Cumming, GA (US)

(73) Assignee: Cingular Wireless II, LLC, Atlanta, GA (US)

( * ) Notice: Subject to any disclaimer, the term of this patent is extended or adjusted under 35 U.S.C. 154(b) by 201 days.

(21) Appl. No.: 11/505,524

(22) Filed: Aug. 16, 2006

(51) Int. Cl.
G08B 25/00 (2006.01)

(52) U.S. Cl. .................. 340/525; 340/531; 340/286.01; 340/825.36; 340/990

(58) Field of Classification Search ......... 340/524–525, 340/506, 988–990, 531, 286.01–286.02, 340/287, 293, 294, 825, 3.1, 825.36; 455/507, 455/517, 521, 404.1–404.2, 403, 422.1
See application file for complete search history.

(56) References Cited

U.S. PATENT DOCUMENTS

| | | | | |
|---|---|---|---|---|
| 5,554,031 A * | 9/1996 | Moir et al. | ................... | 434/111 |
| 5,673,304 A * | 9/1997 | Connor et al. | ................. | 379/45 |
| 6,151,385 A * | 11/2000 | Reich et al. | .................... | 379/49 |
| 6,647,267 B1 * | 11/2003 | Britt et al. | ................. | 455/404.2 |
| 6,775,356 B2 * | 8/2004 | Salvucci et al. | ................ | 379/49 |
| 6,783,492 B2 * | 8/2004 | Dominguez et al. | ......... | 600/365 |
| 7,098,787 B2 * | 8/2006 | Miller | .................... | 340/539.18 |
| 7,149,774 B2 * | 12/2006 | Zellner et al. | ................ | 709/203 |
| 7,289,029 B2 * | 10/2007 | Medema et al. | .......... | 340/573.1 |

* cited by examiner

Primary Examiner—Daniel Previl
(74) Attorney, Agent, or Firm—Woodcock Washburn LLP

(57) ABSTRACT

A device and method for sending medic alert information electronically. The device may have a memory component and a processing component. The memory component may store medic alert information. The processing component may generate an electronic message containing the medic alert information and send the electronic message via a communications network. The device may also have an input component for receiving a user request to initiate a connection with an emergency contact, such as a 911 dispatcher. The electronic message may be automatically generated and sent in response to the user request.

18 Claims, 7 Drawing Sheets

ELECTRONIC MEDIC ALERT

FIELD OF THE INVENTION

Embodiments of the present invention are related generally to a device, system and method for sending medic alert information to an emergency contact and more particularly for sending medic alert information electronically to the emergency contact after a connection with the emergency contact has been initiated.

BACKGROUND OF THE INVENTION

Universal emergency telephone number systems are commonly employed by private and/or public entities to enable individuals to contact local emergency services for assistance. The emergency system may utilize a three-digit number, for example, such that the number is both easy to remember and to dial in case of an emergency. In order to efficiently allocate resources, the emergency system may also assign different numbers for each of the different services that are available. For example, the number "911" may be assigned to emergency medical services, which may be responsible for responding to life-threatening situations (e.g., a heart attack, an automobile accident, a violent crime, etc.), while the number "311" may be assigned to other types of services, which may be responsible for responding to non-life-threatening situations (e.g., a loud neighbor, a stray dog, a street pothole, etc.).

Thus, in the case of a life-threatening emergency, an injured individual seeking immediate medical help may dial 9-1-1 in order to reach an emergency dispatcher. Once connected, the injured individual may convey information regarding the emergency to the dispatcher. For example, the individual may provide his or her identity and present location. The individual may also describe the circumstances that led to the emergency and/or the type of injuries that were sustained. The emergency dispatcher may then contact an emergency medical technician (EMT) to respond to the individual's request for help and relay this information so that the EMT may provide proper medical assistance in a timely manner.

In addition, the emergency dispatcher may also request information from the injured individual associated with his or her medical history. This type of information may be critical in enabling the EMT to provide proper medical assistance. For example, the injured individual may have allergies to one or more medications, such as penicillin, or may currently being taking a medication that causes an adverse reaction when combined with other types of medications. Thus, by being aware of such conditions ahead of time, the EMT may be better prepared, thereby avoiding the potential for further medical complications. However, in many types of emergencies, the emergency dispatcher does not obtain such information because the injured individual is incapable of providing it due to physical or emotional injuries related to the emergency and/or a prior condition. In such situations, the injured individual may only be capable of dialing 9-1-1. Therefore, a need exists for a device, system and method for sending medic alert information electronically to an emergency contact.

SUMMARY OF THE INVENTION

The described embodiments contemplate a device and method for sending medic alert information electronically. The device may be a cellular telephone, for example, and may include a memory component for storing medic alert information and a processing component for generating an electronic message containing the first medic alert information and for sending the electronic message via a communications network. The medic alert information may include the user's name, date of birth, emergency contact information, current medications, known allergies, pre-existing medical conditions, insurance provider, primary care physician, and the like. The device may also include input component (e.g., a keypad) for receiving a user request to initiate a connection with an emergency contact (e.g., a 911 dispatcher). The electronic message may be automatically generated and sent in response to the user request.

The method may include storing medic alert information, initiating a connection with an emergency contact over a communications network, automatically generating an electronic message containing the medic alert information, and sending the electronic message. In another embodiment, the method may include receiving a request from a communications device to establish a connection with an emergency contact, determining a location of the communications device, determining an electronic address of the emergency contact based on the location of the communications device, and routing an electronic message containing medic alert information to the electronic address of the emergency contact, wherein the medic alert information is associated with a subscriber of the communications device.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The foregoing summary, as well as the following detailed description of preferred embodiments, is better understood when read in conjunction with the appended drawings. For the purposes of illustration, there is shown in the drawings example embodiments; however, the invention is not limited to the specific methods and instrumentalities disclosed. In the drawings.

DETAILED DESCRIPTION OF ILLUSTRATIVE EMBODIMENTS

The inventive subject matter is described with specificity to meet statutory requirements. However, the description of the preferred embodiments itself is not intended to limit the scope of this patent. Moreover, although the term "step" may be used herein to connote different elements of methods employed, the term should not be interpreted as requiring any particular order among or between various steps herein disclosed unless otherwise stated.

For purposes of illustration, various embodiments are described herein in connection with the Global System for Mobile Communication (GSM). The references to GSM are not exclusive, however, as it should be appreciated that embodiments may be implemented in connection with any type of wired or wireless access system, such as an intranet, the Internet, a local area network (LAN), a wide area network (WAN), a Public Switched Telephone Network (PSTN), a Code Division Multiple Access (CDMA) network, a Voice Over Internet Protocol (VoIP) network, and the like.

GSM is one of the most widely-used wireless access systems in today's fast growing communication systems. GSM provides circuit-switched data services to subscribers, such as mobile telephone or computer users. General Packet Radio Service (GPRS), which is an extension to GSM technology, introduces packet switching to GSM networks. GPRS uses a packet-based wireless communication technology to transfer high and low-speed data and signaling in an efficient manner. GPRS optimizes the use of network and radio resources, thus enabling the cost effective and efficient use of GSM network resources for packet mode applications.

Figure 1:
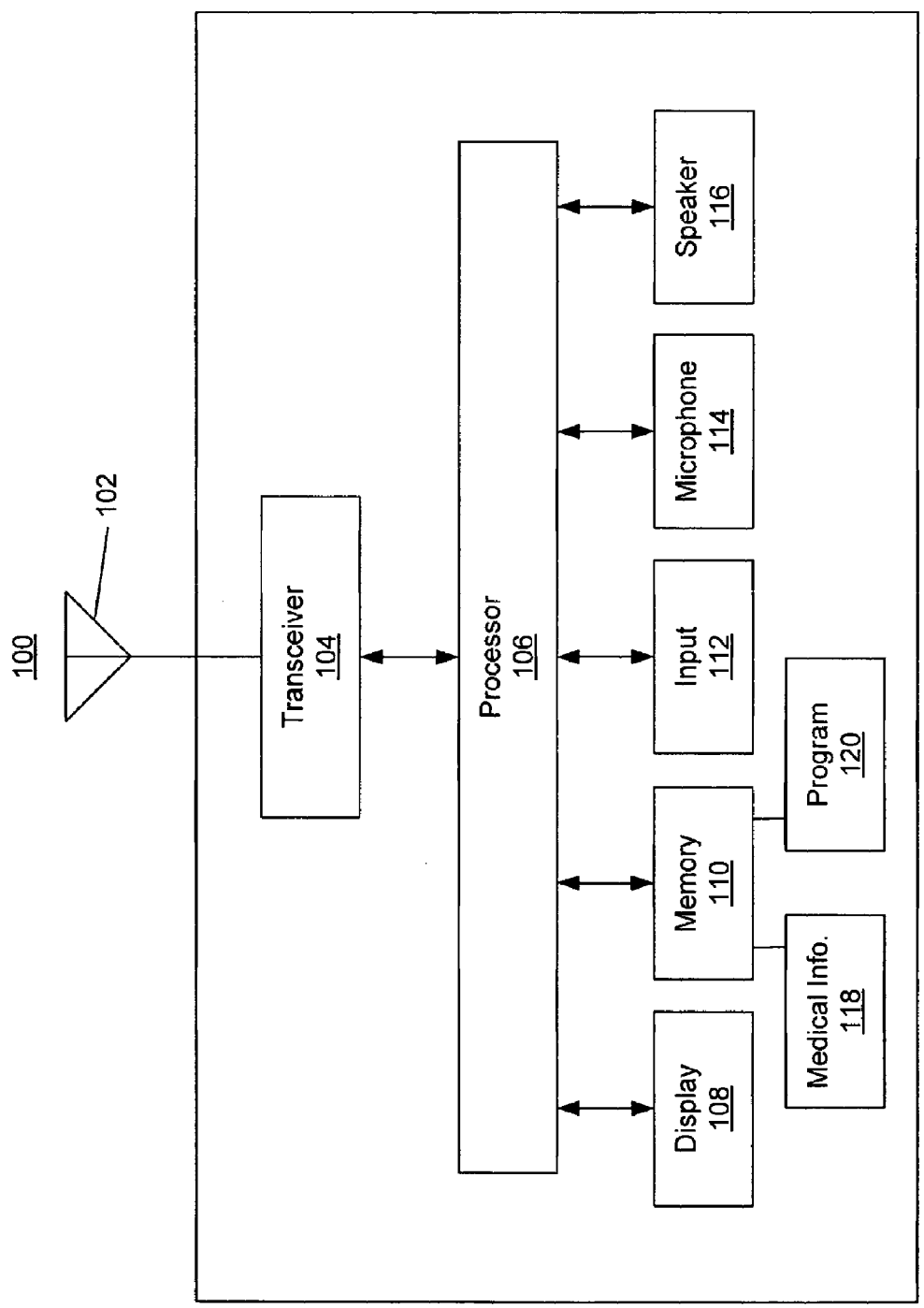
FIG. 1 is a block diagram of an example communications device in which aspects of the invention may be implemented.

FIG. 1 is a block diagram of communications device 100 for communicating in a wireless network, such as a GSM network. Communications device 100 may be adapted to automatically generate and transmit medic alert information 118 electronically to an emergency contact in response to a predetermined user input. Communications device 100 may be any suitable mobile communications device, such as a cellular telephone or a personal digital assistant (PDA), although fixed-line communications devices are also consistent with an embodiment. As shown in FIG. 1, communications device 100 may include transceiver 104, which may transmit and receive wireless signals via antenna 102.

Communications device 100 may include processor 106 and memory 110. Processor 106 may be any suitable processor for operating communications device 100. Memory 110 may include any type of suitable storage device, such as random access memory (RAM), read only memory (ROM), programmable read only memory (PROM), and the like. In addition, memory 110 may be physically integrated into communications device 100 and/or removably attached. For example, communications device 100 may include an integrated internal memory module and/or a Subscriber Identity Module (SIM) card. Memory 110 may store information associated with a user of the device. For example, memory 110 may store user preferences, contact lists, voice messages, text messages, instant messages, email, pictures, video, music, and the like. Memory 110 may also store medic alert information 118 and executable program 120.

Medic alert information 118 may include any type of information that is relevant and/or beneficial in providing medical assistance to the user, such as the user's medical history. By way of example, and not limitation, medic alert information 118 may include the user's name, date of birth, emergency contact information, current medications, known allergies, pre-existing medical conditions, insurance provider, primary care physician, and the like.

Program 120 may include software instructions that can be executed by processor 106 to perform a specific computing task. For example, program 120 may cause processor 106 to automatically generate an electronic message containing medic alert information 118 in response to a predetermined user input or action (e.g., dialing a predetermined number, such as 9-1-1). Program 120 may also cause processor 106 to transmit the electronic message to an emergency contact, such as a 911 dispatcher, for example.

It will be appreciated that memory 110 may store medic alert information 118 for more than one individual, such as each member of a user's family. Medic alert information 118 for each family member may be accessed by inputting a predetermined code before or after dialing 9-1-1. For example, the numbers 1, 2, 3, 4 and 5 may correspond to parent-1, parent-2, child-1, child-2, and child-3, respectively. Thus, if child-2 requires emergency medical assistance, parent-1 may connect to the 911 dispatcher by dialing 4-9-1-1, in which case communications device 100 may generate an electronic message containing medic alert information 118 that pertains to child-2.

Communications device 100 may also include input component 112 (e.g., a keypad, a touch screen, a scroll wheel, a voice recognition module, etc.) and display 108 (e.g., a liquid crystal display). Input component 112 and display 108 may enable a user to enter, access, and/or manipulate information stored in communications device 100. For example, a user of communications device 100 may use input component 112 to enter and store medic alert information 118 into memory 110. Communications device 100 may also include microphone 114 for receiving audio information from the user and speaker 116 for transmitting audio information to the user.

In one embodiment, a user that is in need of immediate medical assistance may initiate a connection to an emergency contact via input component 112. For example, the user may dial 9-1-1 on the keypad of communications device 100 to reach a local 911 dispatcher via a communications network, though the user may dial any predetermined number and may be connected to any public or private entity that is designated as an emergency contact while remaining consistent with an embodiment. Communications device 100 may initiate a voice and/or data connection depending upon the mode in which the user is operating communications device 100. After receiving the 911 input from the user, processor 106 may execute program 120 residing in memory 110, thereby generating an electronic message containing medic alert information 118. Communications device 100 may generate and process the electronic message using any suitable messaging service and/or protocol. For example, communications device 100 may use email, Short Message Service (SMS), Multimedia Message Service (MMS), Session Initiation Protocol (SIP), Instant Messaging (IM), and the like. Processor 106 may then transmit the message to the 911 dispatcher via transceiver 104 and antenna 102.

It will be appreciated that a specific emergency contact (e.g., a 911 dispatcher) may be designated for different geographic areas. Thus, if communications device 100 is a mobile device, the destination of the electronic message may depend upon the geographic location of the device. As will be further discussed below, communications device 100 may therefore generate the electronic message with a predetermined address that corresponds to a predetermined location, such as a server, in the communications network. Based on the location of communications device 100, the communications network may determine the electronic address of the local 911 dispatcher that is associated with that location, assign the address to the electronic message and route the message accordingly. Alternatively, communications device 100 may request the electronic address of the local 911 dispatcher from the communications network prior to transmitting the message.

Figure 2A:
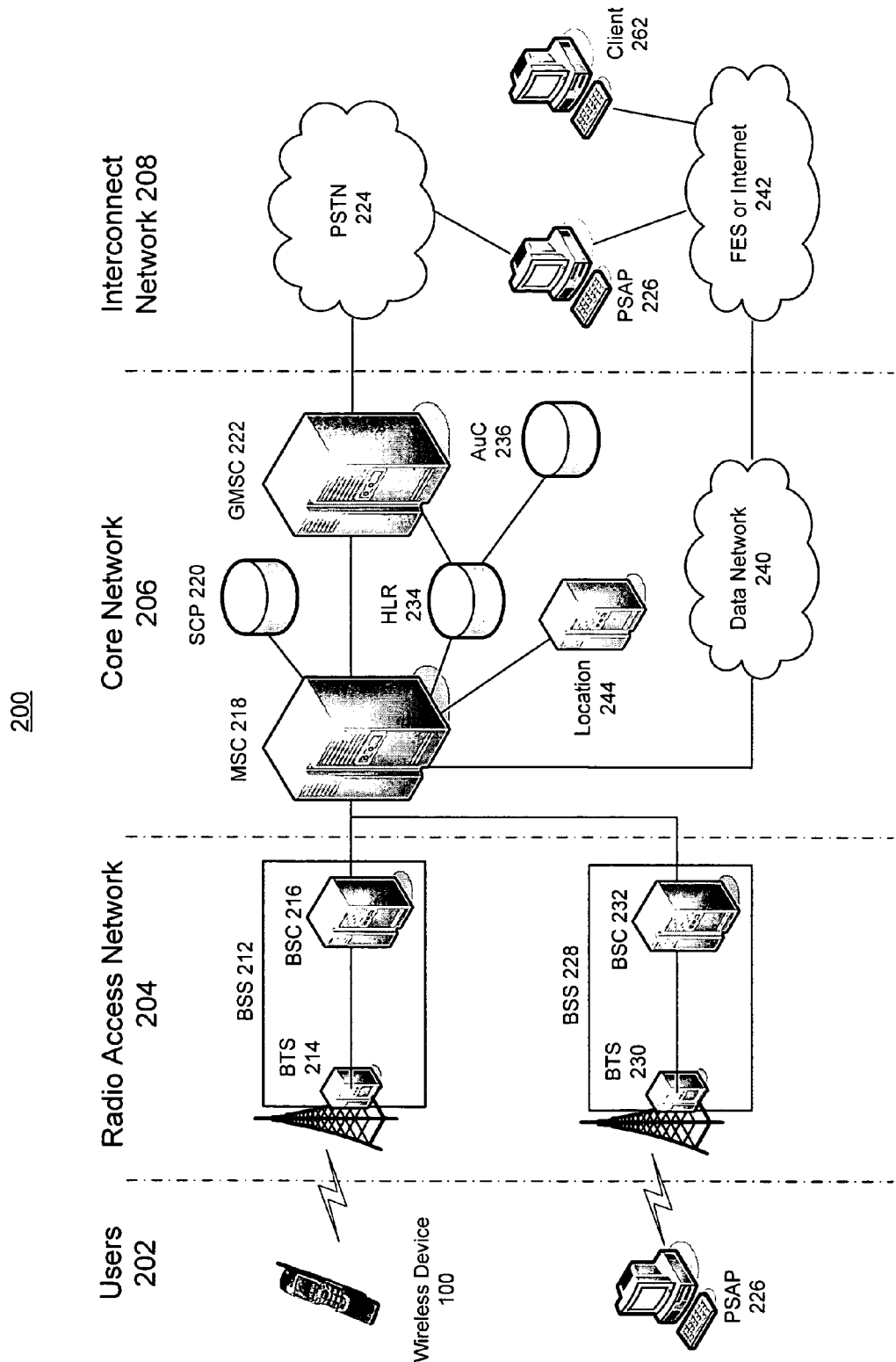
FIG. 2A is a diagram illustrating an example communications network in which aspects of the invention may be implemented.

FIG. 2A illustrates a segmental view of an example communications network 200 that may be adapted to receive an electronic message containing medic alert information 118 from communications device 100 and to route the message to an appropriate emergency contact point. As shown in FIG. 2A, communications network 200 may be a GSM network although other types of networks, such as CDMA, are also consistent with an embodiment. The GSM network may be segmented into four groups: users 202, radio access network (RAN) 204, core network 206, and interconnect network 208. Users 202 may include any number of end users of communications device 100. In addition, users 202 may also include Public Service Access Point (PSAP) 226, which may be a local 911 or 311 dispatcher, though PSAP 226 may also be a for-profit private entity. PSAP 226 may employ any suitable computing and/or telecommunications device for communicating with users 202 via communication network 200.

RAN 204 may include Base Station Subsystems (BSSs) 212, 228, although it will be appreciated that RAN 204 may include any number of such subsystems. BSSs 212, 228 may include Base Transceiver Systems (BTSs) 214, 230 and Base Station Controllers (BSCs) 216, 232, respectively. BTSs 214, 230 may include one or more radio towers that establish a radio interface between users 202 and core network 206. Each BTS may serve more than one user 202. BSCs 216, 232 may manage radio resources, such as BTSs 214, 230, respectively. BSCs 216, 232 may be connected to one or more BTSs.

Core network 206 may include various network elements for processing voice and/or data communications. For example, as shown in FIG. 2A, core network 206 may include Mobile Switching Center (MSC) 218, Service Control Point (SCP) 220, Gateway MSC (GMSC) 222, location server 244, Home Location Register (HLR) 234, Authentication Center (AuC) 236, and data network 240, although other components may also be present. MSC 218 may serve as a switching station for core network 206. SCP 220 may receive and process queries from MSC 218. GMSC 222 may provide a gateway between the GSM network and interconnect network 208, which may include an Integrated Services Digital Network (ISDN), Public Switched Telephone Network (PSTN) 224, and Fixed-End System (FES) or Internet 242. In other words, GMSC 222 may provide interworking functionality with external networks.

MSC 218 may receive traffic from communications device 100 via BSS 212. MSC 218 may determine whether the traffic consists of voice, data, or both. If, for example, the traffic consists of data, MSC 218 may send a query to a database hosted by SCP 220 to determine whether the user of communications device 100 is authorized to send and/or receive data traffic over communications network 200. If, for example, the traffic consists of voice, MSC 218 may send a query to a database hosted by SCP 220 to determine whether the user of communications device 100 is authorized to send and/or receive voice traffic over communications network 200. SCP 220 may process the request and issue a response to MSC 218 authorizing MSC 218 to continue call processing as appropriate. Thus, MSC 218 may separate voice and data traffic such that voice traffic may be routed to ISDN or PSTN 224 through GMSC 222 and data traffic may be routed to FES or Internet 242 through data network 240. As will be further discussed below, data network 240 may include any type and/or number of network elements for processing data traffic.

MSC 218 and SCP 220 may perform other functions as well. For example, SCP 220 may communicate with other intelligent peripherals to play voice messages or to prompt user 202 for information, such as account codes for prepaid long distance cards. MSC 218 may process user registration, authentication, location updating, and handovers. More specifically, HLR 234 may be a central database for all users 202 to register with the GSM network. HLR 234 may store static information about users 202, such as their international mobile subscriber identity (IMSI) number, type of subscribed services and/or authentication key. HLR 234 may also store dynamic information such as the current location of user 202. For example, each time communications device 100 connects with MSC 218 via BTS 214 and BSC 216, MSC 218 may determine the location of communication device 100 by looking up its most current location information stored in HLR 234. Alternatively, MSC 218 may query location server 244, which may be a Gateway Mobile Location Center (GMLC). Location server 244 may provide a position (e.g., latitude/longitude coordinates) of communication device 100 to MSC 218, which may then update the location information stored in HLR 234.

As discussed in the embodiment above, user 202 may initiate a connection with an emergency contact point, such as PSAP 226, over communications network 200 by dialing 9-1-1. The connection may support voice and/or data traffic (e.g., SMS, MMS, instant messaging, etc.). For example, the voice traffic may be received at MSC 218 via BSS 212. MSC 218 may determine the location of communications device 100 by querying HLR 234. Alternatively, MSC 218 may determine the location of communications device 100 by querying location server 244. MSC 218 may then determine which PSAP 226 is responsible for that geographic area and route the voice traffic to PSAP 226 accordingly. As shown in FIG. 2A, the voice traffic may be routed to PSAP 226 via PSTN 224, BSS 228, or FES/Internet 242.

In addition, as noted above, communications device 100 may include program 120, which may enable communications device 100 to automatically generate an electronic message containing medic alert information 118 and transmit the message to a predetermined location in communications network 200. For example, in response to the 9-1-1-input from user 202, communications device 100 may generate and transmit the electronic message to MSC 218 via BSS 212. MSC 218 may then route the message to data network 240, which may include network elements for processing data traffic, such as email, SMS, MMS, instant messaging, SIP, and the like.

Figure 2B:
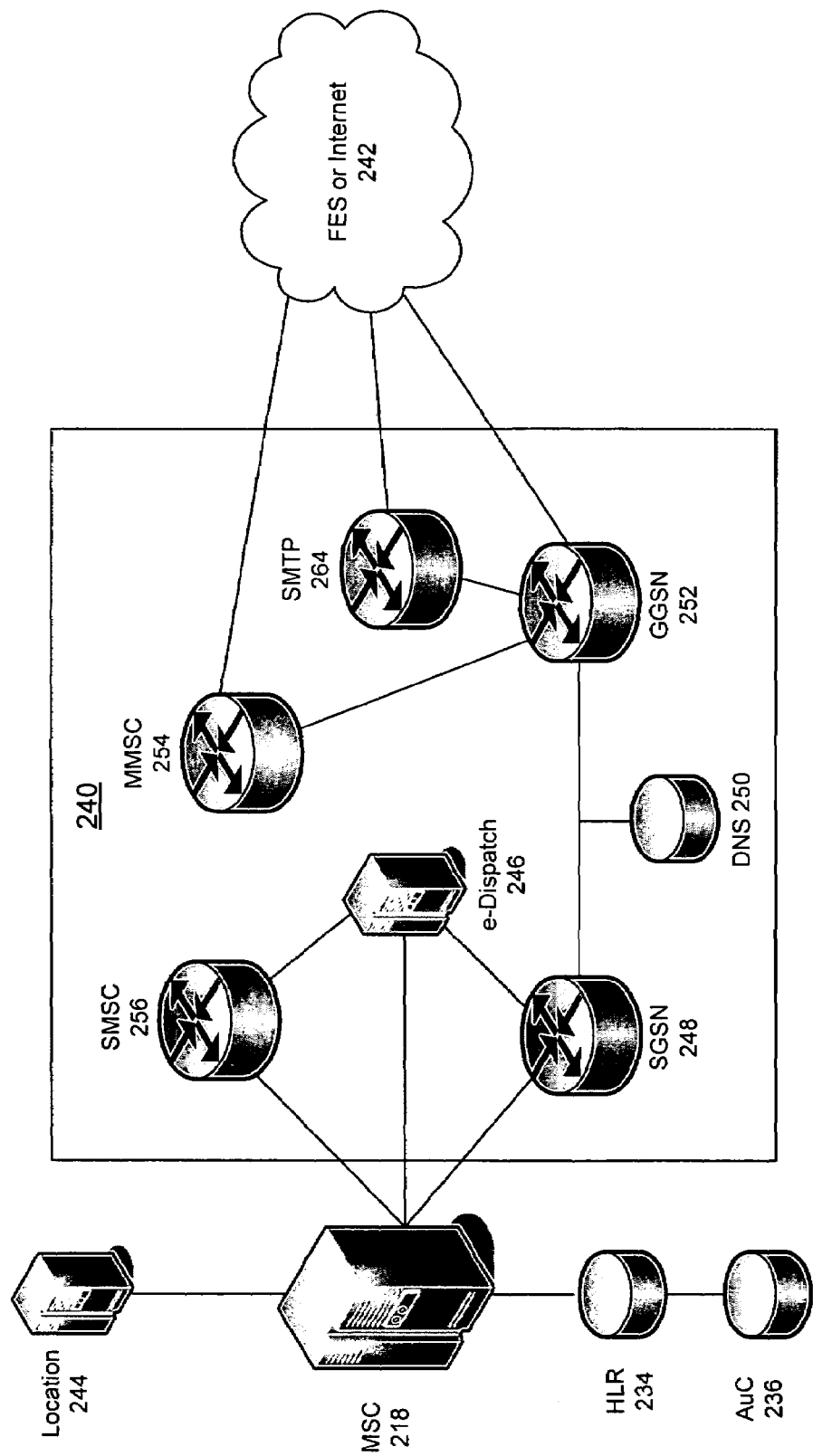
FIG. 2B is a diagram of an example data network within the communications network according to an embodiment.

FIG. 2B is a diagram of an example data network 240. As shown in FIG. 2B, data network 240 may include e-dispatch server 246, Short Message Service Center (SMSC) 256, Service GPRS Support Node (SGSN) 248, Domain Name Service (DNS) 250, Gateway GPRS Support Node (GGSN) 252, Multimedia Messaging Service Center (MMSC) 254, and Simple Mail Transfer Protocol (SMTP) relay 264. Although FIG. 2B depicts data network 240 in communication with a single MSC, it will be appreciated that data network 240 may be connected to any number of MSCs.

In one embodiment, SMSC 256 and e-dispatch server 246 may enable one-to-one SMS messaging between communications device 100 and local PSAP 226. For example, communications device 100 may generate an SMS message containing medic alert information 118. Communications device 100 may assign a predetermined electronic address to the SMS message that corresponds to e-dispatch server 246 in communications network 200. Communications device 100 may then transmit the SMS message to MSC 218. MSC 218 may route the SMS message to e-dispatch server 246, which may contain and access the electronic address information for each PSAP 226 designated in a particular geographic area. Thus, upon receiving the SMS message, e-dispatch server 246 may determine the location of communications device 100 via MSC 218, HLR 234, and/or location server 244 and determine the proper electronic address of PSAP 226 based on the location of communications device 100. E-dispatch server 246 may then assign the proper address to the SMS message and forward the message to SMSC 256, which may then route the SMS message to the appropriate PSAP 226 via PSTN 224, BSS 228, or FES/Internet 242.

In another embodiment, SGSN 248, GGSN 252, MMSC 254 and e-dispatch server 246 may enable one-to-one MMS messaging between communications device 100 and local PSAP 226. For example, communications device 100 may generate an MMS message containing medic alert information 118. Communications device 100 may assign a predetermined electronic address to the MMS message that corresponds to e-dispatch server 246 in communications network 200. Communications device 100 may then transmit the MMS message to MSC 218, which may then route the MMS message to e-dispatch server 246. Upon receiving the MMS message, e-dispatch server 246 may determine the location of communications device 100 via MSC 218, HLR 234, and/or location server 244 and determine the proper electronic address of PSAP 226 based on the location of communications device 100. Server 246 may then assign the proper address to the MMS message and forward the message to SGSN 248, which may control the connection between the GPRS network and communication device 100. SGSN 248 may forward the MMS message to GGSN 252, which may serve as a gateway between the GPRS network and FES or Internet 242. In other words, GGSN 252 may provide interworking functionality with external networks and may set up a logical link to communications device 100 through SGSN 248. GGSN 252 may send the MMS message to MMSC 254, which may then route the MMS message to the appropriate PSAP 226 via PSTN 224, BSS 228, or FES/Internet 242.

In addition to processing text messages, data network 240 may also process emails from communications device 100. Thus, like SMS and MMS messages, emails may also be sent to e-dispatch servers 246, which may determine the proper electronic address of PSAP 226 based on the location of communications device 100. Server 246 may then assign the proper address to the electronic message and forward the message to SMTP relay 264 via SGSN 248 and GGSN 252. SMTP relay 264 may then route the email to the appropriate PSAP 226 via PSTN 224, BSS 228, or FES/Internet 242.

Figure 2C:
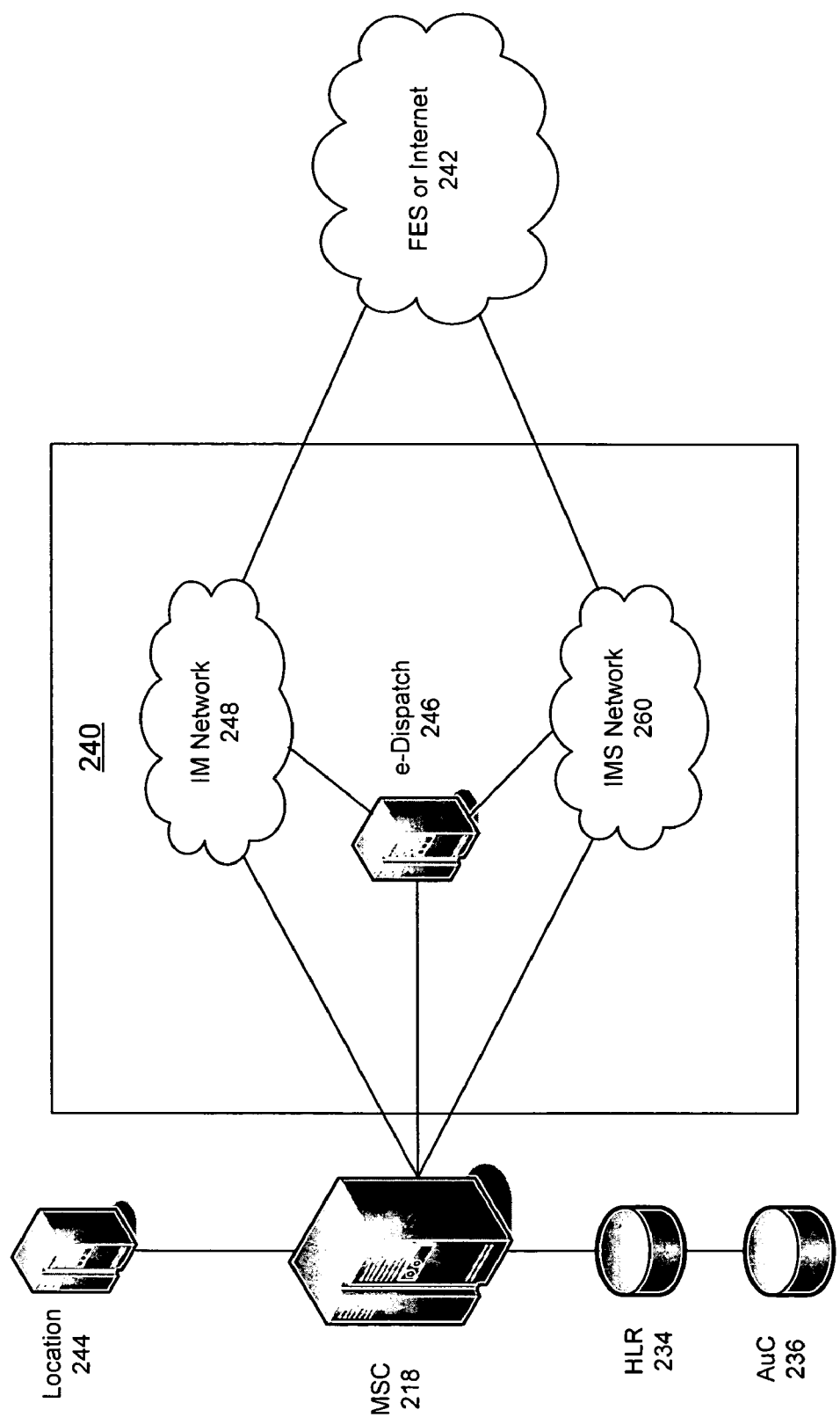
FIG. 2C is a diagram of an example data network within the communications network according to alternative embodiment.

FIG. 2C is a diagram of an alternative example data network 240. As shown in FIG. 2C, data network 240 may include Instant Messaging (IM) network 248 and/or IP Multimedia Subsystem (IMS) network 260. In one embodiment, IMS network 260 and e-dispatch server 246 may enable one-to-one SIP messaging between communications device 100 and local PSAP 226. For example, communications device 100 may generate a SIP message containing medic alert information 118. Communications device 100 may assign a predetermined electronic address to the SIP message that corresponds to e-dispatch server 246 in communications network 200. Communications device 100 may then transmit the SIP message to MSC 218. MSC 218 may route the SIP message to e-dispatch server 246. Upon receiving the SIP message, e-dispatch server 246 may determine the location of communications device 100 via MSC 218, HLR 234, and/or location server 244 and determine the proper electronic address of PSAP 226 based on the location of communications device 100. E-dispatch server 246 may then assign the proper address to the SIP message and forward the message to IMS network 260, which may then route the SIP message to the appropriate PSAP 226 via PSTN 224, BSS 228, or FES/Internet 242.

In another embodiment, IM network 248 and e-dispatch server may enable one-to-one instant messaging between communications device 100 and local PSAP 226. For example, communications device 100 may generate an instant message containing medic alert information 118. Communications device 100 may assign a predetermined electronic address to the instant message that corresponds to e-dispatch server 246 in communications network 200. Communications device 100 may then transmit the instant message to MSC 218. MSC 218 may route the instant message to e-dispatch server 246. Upon receiving the instant message, e-dispatch server 246 may determine the location of communications device 100 via MSC 218, HLR 234, and/or location server 244 and determine the proper electronic address of PSAP 226 based on the location of communications device 100. Server 246 may then assign the proper address to the instant message and forward the message to IM network 248, which may then route the instant message to the appropriate PSAP 226 via PSTN 224, BSS 228, or FES/Internet 242.

It will be appreciated that FIGS. 2B and 2C illustrate example network configurations and that other network configurations may be employed while remaining consistent with an embodiment. For example, although e-dispatch server 246 is shown as a discrete network element in core network 206, its functionality may be incorporated in other existing network elements, such as MSC 218. In addition, e-dispatch server 246 may be implemented in other network environments. For example, e-dispatch server 246, or its functional equivalent, may be implemented in IM network 248 and/or IMS network 260 either in addition to or in lieu of core network 206. Thus, in certain embodiments, MSC 218 may forward the electronic message from communications device 100 to a third-party network (e.g., IM network 248, IMS network 260, etc.) for further processing and routing.

It will further be appreciated that communications device 100 may request the electronic address of the appropriate PSAP 226 from communications network 200 prior to transmitting the electronic message. More specifically, if user 202 dials 9-1-1, for example, communications device 100 may send a request to MSC 218 for the proper electronic address of local PSAP 226 based on the geographic location of communications device 100. MSC 218 may determine the location of communications device 100 via HLR 234 and/or location server 244. MSC 218 may then determine the electronic address of the appropriate PSAP 226 via e-dispatch server 246, or any other suitable database (not shown). MSC 218 may send the electronic address of the appropriate PSAP 226 to communications device 100 via BSS 212. Communications device 100 may assign the electronic address to the electronic message containing medic alert information 118 and transmit the message to MSC 218, which may then route the message to the appropriate PSAP 226 accordingly.

In other embodiments, medic alert information 118 may be stored in e-dispatch server 246 or in one or more databases (not shown) in communications network 200, thereby eliminating the need to store program 120 and/or medic alert information 118 in communications device 100. More specifically, communications network 200 may be adapted to generate and route an electronic message containing medic alert information 118 in response to certain types traffic received from communications device 100. User 202 may access medic alert information 118 stored in communications network 200 via client computer 262. For example, user 202 may use a website accessible on FES or Internet 242 to enter and/or update medic alert information 118.

In one embodiment, e-dispatch server 246 may monitor traffic coming from communications device 100 through the use of a probe. If e-dispatch server 246 detects a certain type of traffic from communications device 100, such as a 911 call, for example, e-dispatch server 246 may identify the user/subscriber of communications device 100 and the location of communications device 100 via MSC 218 and HLR 234. E-dispatch server 246 may then determine the electronic address of the appropriate PSAP 226 based on the location of communications device 100, generate an electronic message containing medic alert information 118 that is associated with user 202, and route the electronic message to the appropriate PSAP 226. In another embodiment, MSC 218 may initiate a CAMEL trigger upon receiving a 911 call, thereby instructing e-dispatch server 246 to generate an electronic message containing the user/subscriber's medic alert information 118 and to route the message to the appropriate PSAP 226 based on the location of communications device 100.

Figure 3:
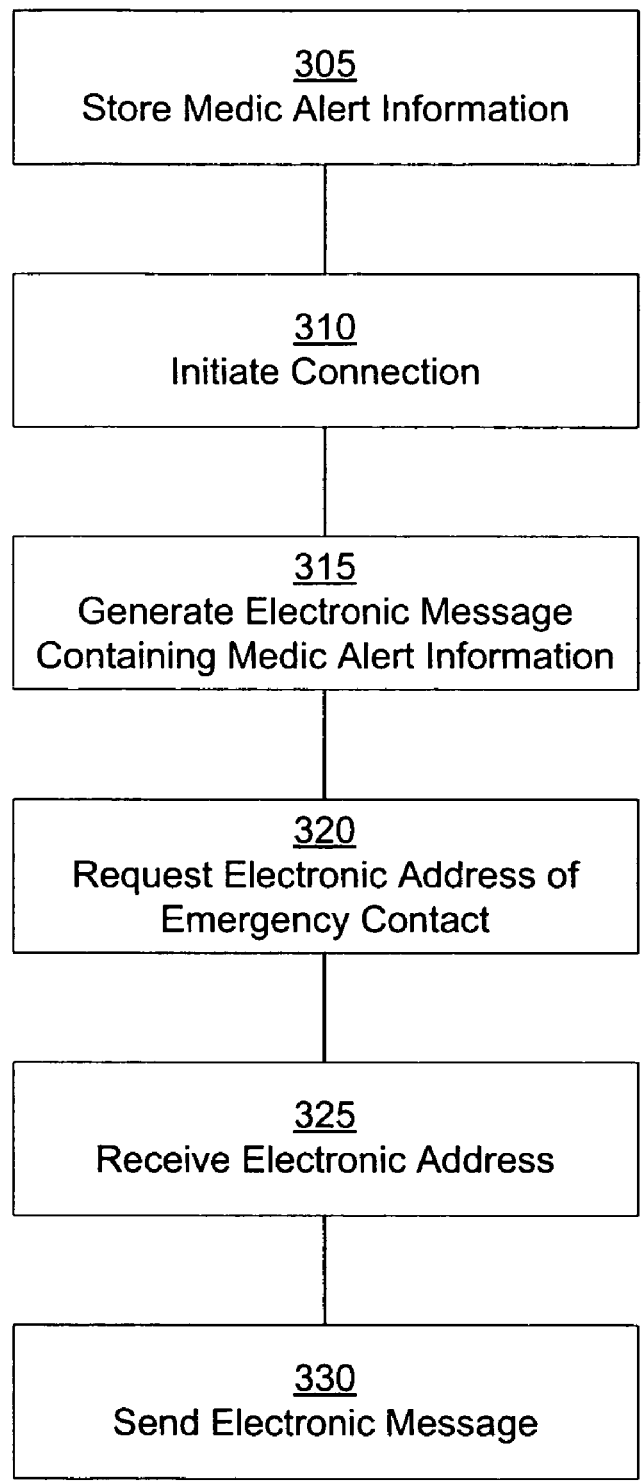
FIG. 3 is a flowchart illustrating an example method for sending medic alert information electronically to an emergency contact via a communications device.

FIG. 3 is a flowchart illustrating an example method for sending medic alert information 118 electronically to PSAP 226 via communications device 100. At 305, medic alert information 118 may be stored in memory 110 of communications device 100. Medic Alert information 118 may be entered into communications device 100 using input component 112. At 310, a user of communications device 100 may initiate a connection with local PSAP 226. For example, as discussed above, the user may need immediate medical assistance and, therefore, may dial 9-1-1. Communications device 100 may initiate a voice and/or data connection over communications network 200 based on its current operating mode (i.e., voice or data mode). At 315, communications device 100 may automatically generate an electronic message containing medic alert information 118. Communications device 100 may generate an email, SMS message, MMS message, SIP message, instant message and/or any other suitable type of message for conveying medic alert information 118.

If communications device 100 is a mobile device, it may be moved to various geographic areas, each with their own PSAP 226. Thus, at 320, communications device 100 may request an electronic address of the appropriate PSAP 226 from communications network 200 based on its current location. At 325, communications device 100 may receive the electronic address of the appropriate PSAP 226 from communications network 200 and assign the address to the electronic message. At 330, communications device 100 may then send the electronic message containing medic alert information 118 to local PSAP 226 via communications network 200.

In an alternative embodiment, communications network 200 may assign the electronic address of local PSAP 226 based on the location of communications device 100. Thus, at 315, communications device 100 may generate an electronic message containing medic alert information 118 and address the message to a predetermined location in communications network 200. For example, as noted above, the electronic message may be addressed and sent to e-dispatch server 246, which may determine the electronic address of the appropriate PSAP 226 based on the location of communications device 100. Accordingly, the process may then proceed from 315 directly to 330, at which communications device 100 may send the electronic message to the predetermined location in communications network 200 for further routing.

Figure 4A:
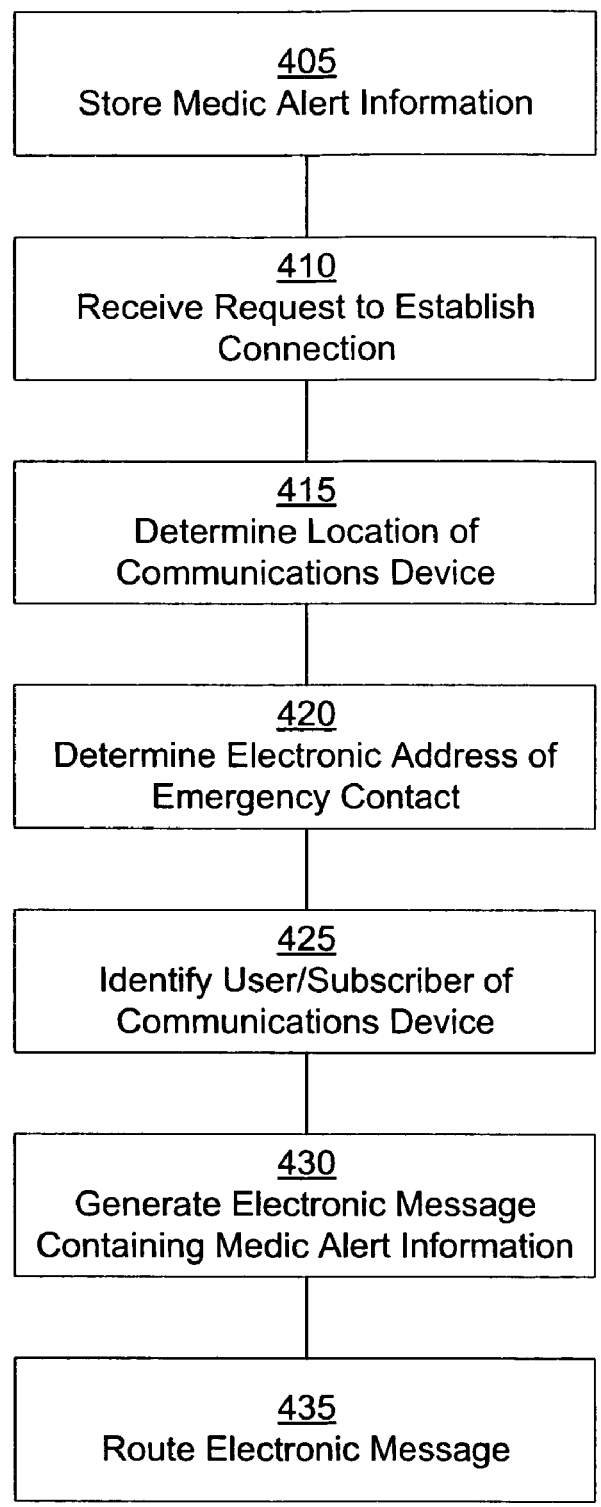
FIGS. 4A and 4B are flowcharts illustrating example methods for sending medic alert information electronically to an emergency contact via a communications network.

FIG. 4A is a flowchart illustrating an example method for sending medic alert information 118 electronically to local PSAP 226 via communications network 200. At 405, communications network 200 may store medic alert information 118 associated with a user and/or subscriber in e-dispatch server 246 and/or in any suitable database. At 410, communications network 200 may receive a request from communications device 100 to establish a connection with PSAP 226. For example, a user of communications device 100 may dial 9-1-1, at which time communications device 100 may send a wireless signal to MSC 218 via BSS 212.

At 415, communications network 200 may determine the location of communications device 100 via MSC 218, HLR 234, and/or location server 244. For example, communications network 200 may determine in which cell communications device 100 is located. At 420, communications network 200 may determine an electronic address of local PSAP 226 based on the geographic location of communications device 100. At 425, communications device 100 may identify the user/subscriber of communications device 100. At 430, communications network 200 may generate an electronic message containing medic alert information 118 of the user/subscriber. At 435, communications network 200 may route the message to PSAP 226.

Figure 4B:
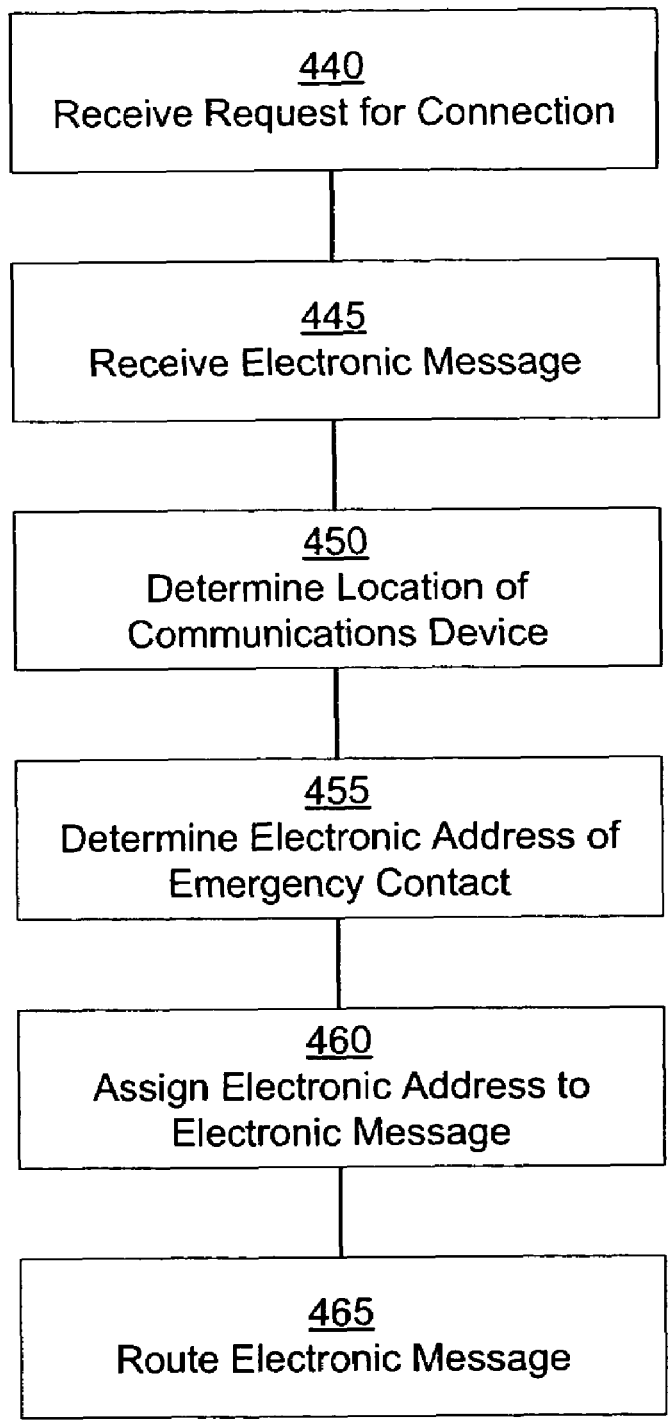

As discussed above, medic alert information 118 may be stored in communications device 100. Thus, FIG. 4B is a flowchart illustrating alternative method for sending medic alert information 118 electronically to local PSAP 226 via communications network 200. At 440, communications network 200 may receive a request from communications device 100 to establish a connection with local PSAP 226. At 445, communications network may receive, at a predetermined location, an electronic message containing medic alert information 118. At 450, communications network 200 may determine a geographic location of communications device 100. At 455, communications network 200 may determine an electronic address of local PSAP 226 based on the location of communications device 100. At 460, communications network 200 may assign the address to the electronic message. At 465, communications network 200 may route the electronic message to the electronic address of local PSAP 226.

While the various embodiments have been described in connection with the preferred embodiments of the various figures, it is to be understood that other similar embodiments may be used or modifications and additions may be made to the described embodiment for performing the same function of the various embodiments without deviating therefrom. Therefore, the embodiments should not be limited to any single embodiment, but rather should be construed in breadth and scope in accordance with the appended claims.

What is claimed is:

1. A mobile communications device for sending medic alert information electronically, comprising:
 a memory component, stored in the mobile communications device, configured to store medic alert information for a plurality of individuals, the medic alert information comprising medical information for each one of the plurality of individuals and a predetermined input code respectably associated with the medical information for each one of the plurality of individuals, the medical information for each one of the plurality of individuals being individually accessible from the memory, wherein the predetermined input code comprises a prefix and a suffix and one of the prefix or the suffix identifies the associated medical information for each one of the plurality of individuals; and
 a processing component, stored in the mobile communications device, configured to, responsive to receiving a selected predetermined input code, generate an electronic message comprising medical information associated with the selected predetermined input code, and to send the electronic message via a communications network.

2. The device of claim 1, further comprising an input component for receiving a user request to initiate a connection with an emergency contact, wherein the electronic message is automatically generated and sent in response to the user request.

3. The device of claim 2, wherein the emergency contact is at least one of a 911 dispatcher and a 311 dispatcher.

4. The device of claim 1, wherein the memory component comprises at least one of a subscriber identity module (SIM) card and an integrated internal memory module.

5. The device of claim 1, wherein the medic alert information comprises a medical history.

6. The device of claim 1, wherein the medic alert information comprises at least one of a name, a date of birth, an age, an emergency contact, an emergency contact number, a known allergy, a preexisting medical condition, a medication, and a primary care physician.

7. The device of claim 1, wherein the electronic message comprises at least one of an email, a short message service (SMS) message, a multimedia message service (MMS) message, an instant message, and a session initiation protocol (SIP) message.

8. The device of claim 1, wherein the processing component sends the message to a predetermined location in the communications network for further routing to an emergency contact that is associated with a geographic area in which the device is located.

9. The device of claim 1, wherein the processing component requests an electronic address of an emergency contact from the communications network, wherein the emergency contact is associated with a geographic area in which the device is located.

10. The device of claim 1, wherein the communications network comprises at least one of an intranet, the Internet, a local area network (LAN), a wide area network (WAN), a public switched telephone network (PSTN), a cellular network, and a voice over internet protocol (VoIP) network.

11. A method for sending medic alert information electronically, comprising:
storing medic alert information for a plurality of individuals in a memory component of a mobile communications device, the medic alert information comprising medical information for each one of the plurality of individuals and a predetermined input code respectably associated with the medical information for each one of the plurality of individuals, the medical information for each one of the plurality of individuals being individually accessible from the memory component, wherein the predetermined input code comprises a prefix and a suffix and one of the prefix or the suffix identifies the associated medical information for each one of the plurality of individuals;
initiating a connection with an emergency contact over a communications network;
responsive to receiving a selected predetermined input code, generating an electronic message comprising medical information associated with the selected predetermined input code; and
sending the electronic message.

12. The method of claim 11, wherein the electronic message is sent to a predetermined location in the communications network for further routing to the emergency contact and wherein the emergency contact is associated with a geographic area in which the electronic message was generated.

13. The method of claim 11, further comprising requesting an electronic address of the emergency contact from the communications network, wherein the emergency contact is associated with a geographic area in which the electronic message was generated.

14. A method for sending medic alert information electronically, comprising:
receiving a request from a mobile communications device to establish a connection with an emergency contact;
determining a location of the mobile communications device;
determining an electronic address of the emergency contact based on the location of the communications device; and
routing over a communications network an electronic message, generated responsive to receiving a selected predetermined input code, containing medic alert information to the electronic address of the emergency contact, the medic alert information comprising medical information for each one of a plurality of individuals and the predetermined input code respectably associated with the medical information for each one of the plurality of individuals, wherein the predetermined input code comprises a prefix and a suffix, wherein either the prefix or the suffix identifies the associated medical information for each one of the plurality of individuals, wherein the medic alert information is stored in a memory component of a mobile communications device, the medical information for each one of the plurality of individuals being individually accessible from the memory, wherein the medic alert information is associated with an individual other than a subscriber of the communications device.

15. The method of claim 14, further comprising storing the medic alert information.

16. The method of claim 14, further comprising identifying the subscriber of the communications device and automatically generating the electronic message after receiving the request from the communications device.

17. The method of claim 14, further comprising receiving the electronic message from the communications device.

18. The method of claim 14, further comprising sending the electronic address of the emergency contact to the communications device.

* * * * *